(12) United States Patent
Bloch

(10) Patent No.: US 10,864,489 B2
(45) Date of Patent: Dec. 15, 2020

(54) APPARATUS AND METHOD FOR PROVIDING ASYMMETRIC OSCILLATIONS

(71) Applicant: Andrew E. Bloch, Las Vegas, NV (US)

(72) Inventor: Andrew E. Bloch, Las Vegas, NV (US)

( * ) Notice: Subject to any disclaimer, the term of this patent is extended or adjusted under 35 U.S.C. 154(b) by 710 days.

(21) Appl. No.: 15/489,507

(22) Filed: Apr. 17, 2017

(65) Prior Publication Data

US 2017/0216793 A1 Aug. 3, 2017

Related U.S. Application Data

(63) Continuation of application No. 14/177,844, filed on Feb. 11, 2014, now Pat. No. 10,058,833.
(Continued)

(51) Int. Cl.
*B01F 11/00* (2006.01)
*G01N 15/10* (2006.01)
(Continued)

(52) U.S. Cl.
CPC .......... *B01F 11/0097* (2013.01); *A23G 9/224* (2013.01); *A61B 8/54* (2013.01); *B01F 3/0819* (2013.01); *B01F 11/004* (2013.01); *B01F 11/0031* (2013.01); *B01F 11/0283* (2013.01); *B01F 15/00129* (2013.01); *B01F 15/00201* (2013.01); *B01F 15/00331* (2013.01); *B01F 15/00746* (2013.01); *B01J 8/40* (2013.01); *B01J 19/008* (2013.01); *B01J 19/285* (2013.01);
(Continued)

(58) Field of Classification Search
CPC .............. B01F 11/0283; B01F 11/0097; B01F 3/0819; B01F 11/0031; B06B 3/02; G01N 2035/00554; G01N 15/10; G01N 29/14; B01J 19/285; G01M 7/022; H01M 10/44; H01M 2010/4292; A23G 9/224; A61B 8/54
See application file for complete search history.

(56) References Cited

U.S. PATENT DOCUMENTS 2,766,681 A 10/1956 Rigo
2,766,881 A 10/1956 Westervelt
(Continued)

FOREIGN PATENT DOCUMENTS

CN 102065970 5/2011
CN 105008006 10/2015
(Continued)

OTHER PUBLICATIONS

Japanese Patent Application 2015-557197 Notice of Allowance dated Mar. 6, 2018.
(Continued)

*Primary Examiner* — Anshu Bhatia
(74) *Attorney, Agent, or Firm* — Polsinelli LLP

(57) ABSTRACT

Disclosed is an apparatus and method for providing asymmetric oscillations to a container. The container may include a fluid, a particle, and/or a gas. A vibration driver attached to the container provides asymmetric oscillations. A controller connected to the vibration driver controls an amplitude, frequency, and shape of the asymmetric oscillations. An amplifier amplifies the asymmetric oscillations in response to the controller. A sensor disposed on the vibration driver provides feedback to the controller.

29 Claims, 3 Drawing Sheets

Related U.S. Application Data

(60) Provisional application No. 61/763,029, filed on Feb. 11, 2013.

(51) Int. Cl.

| | | |
|---|---|---|
| *A61B 8/00* | (2006.01) | |
| *G01N 29/14* | (2006.01) | |
| *G01M 7/02* | (2006.01) | |
| *B01F 15/00* | (2006.01) | |
| *A23G 9/22* | (2006.01) | |
| *B01F 11/02* | (2006.01) | |
| *B01J 8/40* | (2006.01) | |
| *B01J 19/00* | (2006.01) | |
| *B01J 19/28* | (2006.01) | |
| *H01M 10/44* | (2006.01) | |
| *B01F 3/08* | (2006.01) | |
| *H01M 10/42* | (2006.01) | |

(52) U.S. Cl.
CPC ............ *G01M 7/022* (2013.01); *G01N 15/10* (2013.01); *G01N 29/14* (2013.01); *H01M 10/44* (2013.01); *B01F 2215/0021* (2013.01); *B01F 2215/0034* (2013.01); *B01F 2215/0036* (2013.01); *B01F 2215/0037* (2013.01); *B01J 2208/00796* (2013.01); *B01J 2208/00823* (2013.01); *B01J 2219/00189* (2013.01); *G01N 2015/1075* (2013.01); *H01M 2010/4292* (2013.01)

(56) References Cited

U.S. PATENT DOCUMENTS

| | | | |
|---|---|---|---|
| 3,325,386 | A | 6/1967 | Woldemar |
| 3,381,525 | A | 5/1968 | Kartluke et al. |
| 3,614,069 | A | 10/1971 | Murry |
| 3,915,890 | A | 10/1975 | Soldate |
| 5,449,493 | A | 9/1995 | Rokugawa et al. |
| 5,523,058 | A * | 6/1996 | Umemura ............... A61N 7/02 134/1 |
| 5,872,443 | A | 2/1999 | Williamson |
| 7,338,586 | B2 | 3/2008 | Omasa |
| 7,448,792 | B2 | 11/2008 | Tessien |
| 7,686,500 | B2 * | 3/2010 | Laugharn, Jr. .......... B01F 11/02 366/127 |
| 8,960,992 | B2 | 2/2015 | Jong et al. |
| 10,058,833 | B2 | 8/2018 | Bloch |
| 10,058,834 | B2 | 8/2018 | Bloch |
| 2005/0142664 | A1 | 6/2005 | Loney |
| 2008/0170464 | A1 | 7/2008 | Murakami |
| 2008/0225634 | A1 | 9/2008 | Murakami |
| 2009/0074621 | A1 | 3/2009 | Murakami |
| 2009/0092518 | A1 | 4/2009 | Murakami |
| 2009/0168591 | A1 | 7/2009 | Wenzel et al. |
| 2009/0262597 | A1 | 10/2009 | Keiffer et al. |
| 2010/0135104 | A1 | 6/2010 | Schoenfeld |
| 2010/0150859 | A1 | 6/2010 | Do et al. |
| 2011/0163013 | A1 | 7/2011 | Lurz et al. |
| 2011/0176964 | A1 | 7/2011 | Murakami |
| 2014/0226430 | A1 | 8/2014 | Bloch |
| 2017/0056849 | A1 | 3/2017 | Bloch |
| 2020/0129936 | A1 | 4/2020 | Bloch |
| 2020/0129937 | A1 | 4/2020 | Bloch |
| 2020/0129938 | A1 | 4/2020 | Bloch |
| 2020/0129939 | A1 | 4/2020 | Bloch |

FOREIGN PATENT DOCUMENTS

| | | |
|---|---|---|
| EP | 1 260 819 | 11/2002 |
| EP | 1 894 617 | 3/2008 |
| EP | 2 388 067 | 11/2011 |
| EP | 2 953 710 | 12/2015 |
| GB | 2 173 420 | 10/1986 |
| JP | 07-047259 | 2/1995 |
| JP | 09-122480 | 5/1997 |
| JP | 2010-515565 | 5/2010 |
| WO | WO 2008/088321 | 7/2008 |
| WO | WO 2014/124440 | 8/2014 |

OTHER PUBLICATIONS

U.S. Appl. No. 14/177,844 Office Action dated Dec. 20, 2017.
U.S. Appl. No. 15/348,775 Office Action dated Dec. 22, 2017.
Chinese Patent Application No. 201480014585.0 First Office Action dated Jun. 29, 2016.
European Patent Application No. 14748721.9 Extended European Search Report dated Nov. 10, 2016.
PCT Application No. PCT/US2014/015804 International Search Report and Written Opinion dated Sep. 14, 2015.
U.S. Appl. No. 14/177,844 Final Office Action dated Apr. 5, 2017.
U.S. Appl. No. 14/177,844 Office Action dated Jul. 14, 2016.
U.S. Appl. No. 15/348,775 Office Action dated Jan. 12, 2017.
Chinese Patent Application No. 201480014585.0 2nd Office Action dated May 11, 2017.
U.S. Appl. No. 15/348,775 Final Office Action dated Jun. 2, 2017.
U.S. Appl. No. 16/731,836, Andrew E. Bloch, Apparatus and Method for Providing Asymmetric Oscillations, filed Dec. 31, 2019.
U.S. Appl. No. 16/731,857, Andrew E. Bloch, Apparatus and Method for Providing Asymmetric Oscillations, filed Dec. 31, 2019.
U.S. Appl. No. 16/731,883, Andrew E. Bloch, Apparatus and Method for Providing Asymmetric Oscillations, filed Dec. 31, 2019.
U.S. Appl. No. 16/731,900, Andrew E. Bloch, Apparatus and Method for Providing Asymmetric Oscillations, filed Dec. 31, 2019.
Japanese Patent Application 2015-557197 Office Action dated Oct. 3, 2017.
U.S. Appl. No. 14/177,844 Final Office Action dated Sep. 5, 2017.
U.S. Appl. No. 15/348,775 Final Office Action dated Sep. 15, 2017.
U.S. Appl. No. 16/731,836 Office Action dated Apr. 1, 2020.
U.S. Appl. No. 16/731,857 Office Action dated Apr. 1, 2020.
U.S. Appl. No. 16/731,883 Office Action dated Apr. 1, 2020.
U.S. Appl. No. 16/731,900 Office Action dated Apr. 1, 2020.
U.S. Appl. No. 16/731,836 Final Office Action dated Jul. 28, 2020.
U.S. Appl. No. 16/731,857 Final Office Action dated Jul. 29, 2020.
U.S. Appl. No. 16/731,883 Final Office Action dated Jul. 29, 2020.

* cited by examiner (a) Acceleration of container (b) Velocity of particle relative to container (particle denser than fluid)

(a)

(b)

(c)

APPARATUS AND METHOD FOR PROVIDING ASYMMETRIC OSCILLATIONS

CROSS-REFERENCE TO RELATED APPLICATIONS

The present patent application is a continuation and claims the priority benefit of U.S. patent application Ser. No. 14/177,844 filed Feb. 11, 2014, which claims the priority benefit of U.S. provisional patent application No. 61/763,029 filed Feb. 11, 2013, the disclosures of which are incorporated by reference herein.

BACKGROUND OF THE INVENTION

Field of the Invention

The present invention is generally related to levitating, suspending, moving, fluidizing, or mixing solid particles or fluid bubbles in a fluidic environment. More specifically, the present invention is related to an apparatus and method for levitating, suspending, moving, fluidizing, or mixing solid particles or fluid bubbles in a fluidic environment by suitable non-sinusoidal vibration.

Description of the Related Art

There are several existing methods for levitating or suspending particles in a fluid (liquid or gas). Levitation methods include using electromagnetic, electrostatic, acoustic, and aerodynamic forces. Electromagnetic and electrostatic methods can only levitate materials having the right electromagnetic properties and cannot levitate gas bubbles within a fluid. Acoustic levitation methods work with a wider range of material, but the material is only be levitated at specific acoustic nodes, and not dispersed throughout a volume. Aerodynamic levitation requires a net upwards directional flow of air or other fluid to keep particles suspended, and cannot simultaneously levitate gas bubbles and solid particles within a fluid.

The suspension of multiple particles in a fluid, also called fluidization, can also be achieved by vibration of a container or fluid at accelerations above gravity. When low frequency vibration is used, particles are imparted energy primarily through collisions with the bottom of the container or collisions with other particles. Ultrasonic vibrations transmit energy by sound waves through the bulk fluid which can accelerate particles and keep them suspended, or achieve a level of homogenization of a liquid that persists long after the vibrations ended. However, the energy required can be high if the particles are large or dense, and cavitation, which may be undesirable, often occurs.

Since the 1950s or earlier, it has been known that gas bubbles can be levitated in a liquid that is subjected to low frequency (about 100 Hz) vertical vibrations. The levitation is thought to be due in part to the bubble volume oscillating as it moves up and down within the liquid. The solutions to the force equations in the literature on this subject predict that a bubble will levitate at a certain height from the top of the liquid, depending on the oscillation frequency and other factors, but not the amplitude (as long as the amplitude of the acceleration is somewhat greater than the acceleration due to gravity). However, researchers have found that the amplitude of vibration does have some influence, though they have not yet explained why.

Prior researchers have made assumptions about the drag force acting on the air bubbles (or ignored drag altogether), leading to the erroneous conclusion that the drag force itself does not affect the levitation. However, drag forces acting on the bubbles can be complicated and are generally not linearly related to velocity. In particular, as the amplitude of vibration is increased, the maximum velocity of the bubbles can increase into the region where drag forces are more proportional to the square of the velocity. In other words, the bubbles had a high Reynolds number. Researchers have also not considered the effect of non-sinusoidal vibrations, possibly because they have assumed incorrectly that the response is linear.

The current general-purpose vibration testing procedures are single frequency tests, swept sine tests, random tests, and drop or impulse tests. These tests are insufficient to uncover significant defects (or features) which can be caused by non-linear vibration responses to some real-world non-sinusoidal vibrations. Vibration testing can be greatly improved by utilizing non-sinusoidal vibrations that enhances or exposes the non-linear vibration response. One particular industry that can greatly benefit from improved vibration testing is the aerospace industry, including battery systems, on-board fuel storage and delivery systems, and other multi-phase systems. The lack of adequate vibration testing has had severe results, resulting in aerospace disasters and costly grounding of aircraft.

Current devices and methods for the research or use of cavitation have a limited ability to control the strength or likelihood of cavitation independent of the other effects of vibration. Typically, an ultrasonic transducer driven with a single frequency is immersed in a fluid and the effects of sonication are concentrated near the surface of the transducer. Cavitation can be reduced or eliminated by reducing power or other parameters, reducing other desired effects of sonication. To achieve single bubble sonoluminescence, researchers commonly levitate and stabilize a single bubble via acoustic pressure standing waves which requires very specific driving frequencies. Another method developed more recently achieves stable sonoluminescence using a "water hammer tube" approximately half full with liquid. Driven externally with a single frequency, some bubbles are entrained and experience "negative" buoyancy, dropping to the bottom of the tube. This effect cannot be controlled without changing the frequency or amplitude of the vibrations, which affects the size and sonoluminescence of the bubbles.

Current devices for approximating the effects of microgravity under Earth gravity include drop towers, parabolic flights, and clinostats. Drop towers and parabolic flights only allow short periods of microgravity, up to about 20 seconds. Parabolic flights are expensive and limited to experiments that are safe to perform on an airplane. The best drop towers only give a period of about 10 seconds, with only a few repetitions possible per day, and high decelerations at the bottom limit the types of experiments that can be performed. Clinostats use rotation about a horizontal axis (or random rotation) so the time-averaged acceleration due to gravity is zero. Long experiments can be performed on clinostats, but this technique only works for items which respond slowly to acceleration, such as plants.

Current medical ultrasonography devices use a single frequency and measure the time and amplitude of echos to form an image inside the human body. Although generally considered safe, some studies have found weak, but statistically significant effects on children exposed to ultrasound in the womb. As a result, the FDA has established guidelines limiting the acoustic power using several metrics, primarily the Thermal Index (TI), which measures the potential for tissue heating, and the Mechanical Index (MI), which measures the risk of cavitation and, to a lesser degree, streaming.

Embodiments of the present invention include an apparatus and method to levitate, suspend, or mix particles or bubbles in a fluid, or to mix two or more fluids or granular materials, using of asymmetric vertical vibrations that nullify, reverse, or enhance the effect of gravity. Embodiments of the present invention can improve chemical reactions and other processes, and make new ones possible. Embodiments of the present invention can also be used to position particles or counteract the effect of residual acceleration in a microgravity environment. One embodiment of the present invention includes an apparatus and method for improved vibration testing. Another embodiment of the present invention is also an apparatus and method using vibration to improve batteries.

SUMMARY OF THE CLAIMED INVENTION

An apparatus for providing asymmetric oscillations is recited in a first claimed embodiment. The apparatus includes a container. A fluid and a particle are disposed within the container. A vibration driver attached to the container oscillates the container to impart asymmetric velocity to the particle by way of the fluid.

A second claimed embodiment recites a method of providing asymmetric oscillations on a container. The method includes the steps of disposing a fluid and a particle in the container. Asymmetrical motion is imparted on the particle through the fluid by way of a vibration driver attached to the container. Non-linear drag force is leveraged on the particle.

Further scope of applicability of the present invention will be set forth in part in the detailed description to follow. Taken in conjunction with the accompanying drawings and the knowledge of one of ordinary skill in the art, various advantages may be realized and attained by means of the instrumentalities and combinations, including those set forth in the appended claims.

BRIEF DESCRIPTION OF THE DRAWINGS

The accompanying drawings are incorporated into and form a part of the specification. The drawings illustrate one or more embodiments of the present invention. Together with the description, the drawings serve to explain various aspects of the invention. The drawings are only for the purpose of illustrating one or more embodiments and not for the purpose of limiting the invention.

DETAILED DESCRIPTION

Embodiments of the present invention are related to an apparatus and method for levitating, suspending, moving, fluidizing, or mixing solid particles or fluid bubbles in a fluidic environment, and specifically to an apparatus and method for levitating, suspending, moving, fluidizing, or mixing solid particles or fluid bubbles in a fluidic environment by suitable non-sinusoidal vibration.

Embodiments of the present invention also relate to an apparatus and method for vibration testing, particularly testing of systems involving a fluidic environment having solid or fluid particles as well as an apparatus and method to create cavitation at a wide range of vibration frequencies, pressures, and bubble sizes, than has been possible with prior art, and control, increase, reduce, or eliminate cavitation at both low and high frequencies, while controlling, increasing, reducing, or eliminating other effects of vibration.

Embodiments of the present invention also relate to an apparatus and method that allow for improved research into the phenomenon of cavitation and the possibility of bubble fusion; an apparatus and method for testing the effects of microgravity or partial gravity within an environment subject to a possibly different inertial force; an apparatus and method to study, improve, control, and model crystallization, solidification (e.g., of alloys and glasses), peptization, flocculation, gelation, the sol-gel process, polymerization, foaming, acoustic streaming, mass transfer, reaction rates, and similar processes, through non-sinusoidal vibrations, particularly at low frequencies; an apparatus and method to increase the current that a battery can supply, or the charging speed of a battery, through the application of sinusoidal or non-sinusoidal vibrations; and an apparatus and method to improve and study ultrasound, including medical ultrasound, by controlling, reducing, increasing, or eliminating cavitation, streaming, and other desired or undesired effects as well as controlling, reducing, increasing, or eliminating convection and improving combustion.

As used throughout the specification and claims, the terms vibrations and oscillations are used interchangeably. The term particle can include, but is not limited to a bubble, for example, an air bubble or a gas bubble or a liquid bubble, a solid portion of matter having any shape including but not limited to spherical, conical, cylindrical, cubical, combinations thereof and the like. The term fluid is defined as any substance that has no fixed shape, for example, a liquid or a gas or a combination of a liquid and gas.

Figure 1:
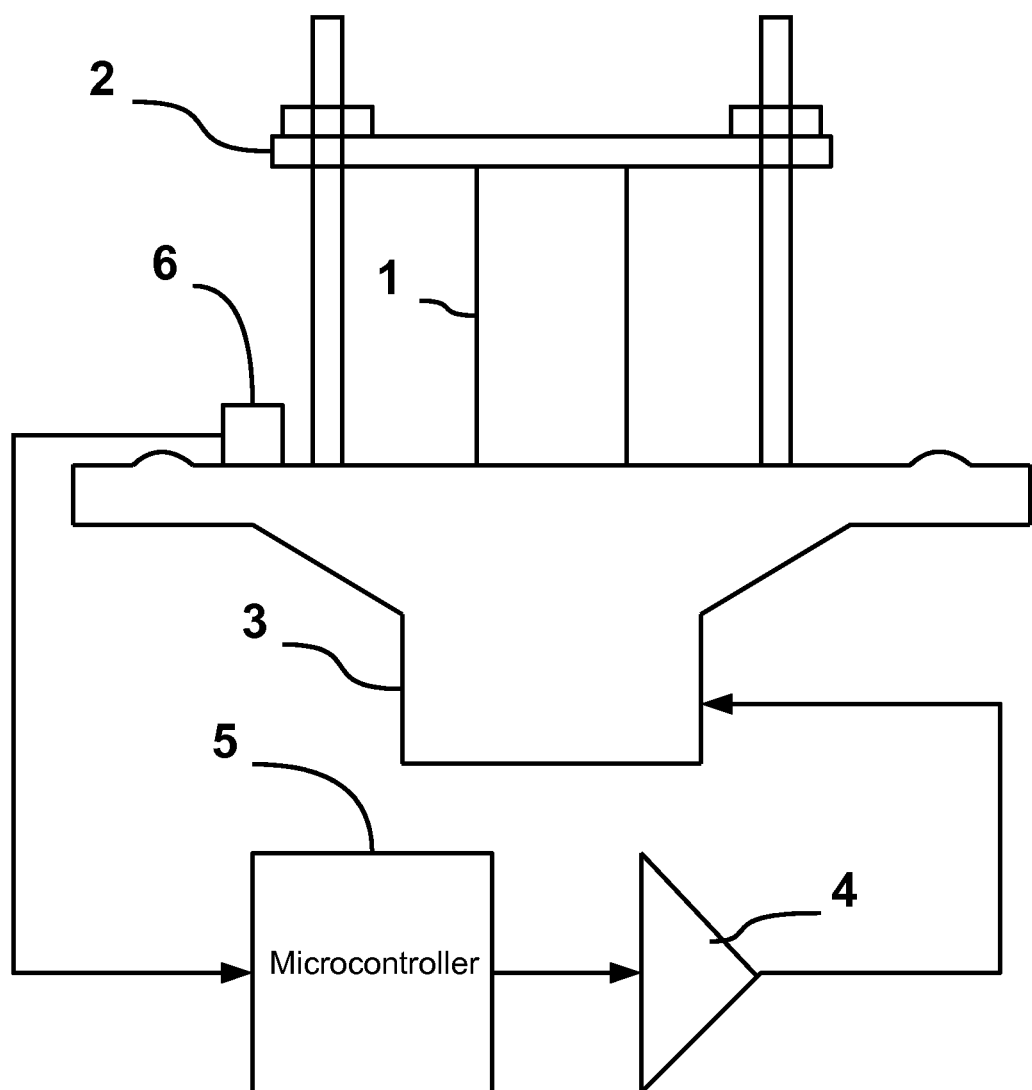
FIG. 1 is a side view of an embodiment of the present invention.

FIG. 1 illustrates an embodiment of the invention that includes container 1 having the fluids that are mixed, or the fluid and the particles that are levitated within the fluid, or multiple fluids and particles. Particles are typically on the order of a millimeter in diameter but they can be as small as a molecule, or much larger than a millimeter in diameter. There is no limit to the size of the particle, if an apparatus can be built big enough to vibrate over a large enough distance.

Brace 2 attaches container 1 to vibration driver 3. Power amplifier 4 amplifies the drive waveform from microcontroller 5 to power vibration transducer 3. Accelerometer 6 provides acceleration feedback to microcontroller 5 which can then modify the drive waveform in response to the feedback. In one embodiment, microcontroller 5 uses Fourier analysis of the signal from accelerometer 6 to determine how to adjust the drive waveform to achieve the desired vibration. If desired, microcontroller 5 outputs data to another microcontroller or computer (not shown) monitoring the process. If flexibility is not needed, once a suitable drive waveform is found, the microcontroller 5 and accelerometer 6 can be replaced with any device that can output a repeating electronic waveform. In addition to, or in the alternative, to accelerometer 6, there can be other observation or feedback mechanisms such as acoustical, optical, electromagnetic, physical, or chemical sensors. For example, an optical sensor or camera can determine if opaque particles are being levitated, and electrically-charged probes inside the container can detect when particles which can hold an electric charge touch the probes. Acoustic (vibration) transducers, which generally have a higher frequency response than accelerometers, are often the best sensors for detecting cavitation collapse.

Container 1 can be of many different types, shapes, and materials. It can be a closed container, for batch-type operation, or connected to a larger system through connectors or valves for operation in a continuous or semi-continuous mode. In one embodiment, the sides of container 1 are vertical and the top and bottom are flat, but other shapes are possible and may be preferred, causing different mixing patterns, the magnification of motion, or the stabilization of particles or bubbles, among other effects.

Vibration transducer 3 can be a regular audio speaker driver, a linear motor, a rotary motor with circular motion converted to linear motion using gears, linkages, cams, or other mechanisms, or any other device capable of large and fast enough vibrations. If flexibility is desired, a transducer with a wide frequency range is preferred. If the apparatus is to be used for a specific purpose that does not require flexibility in the waveform, then one embodiment of the invention can incorporate a vibration transducer designed to produce asymmetric accelerations efficiently, through appropriate mechanisms, such as asymmetric springs, cams, or other mechanisms, or the combination of two or more harmonically-related sinusoidal oscillators. In one non-limiting example, a speaker driver with a spider and surround is used and acts as an asymmetric spring mechanism, with a higher spring constant in the bottom portion of the motion than the top portion. A second example of a vibration driver is a circular motor with a cam designed to give higher acceleration for a shorter period and lower acceleration for a longer period. A third example of a vibration transducer is the combination of two piezoelectric oscillators, one oscillating with a frequency twice the other with half the amplitude of acceleration, with the correct phase relationship (the maxima of the acceleration of the higher frequency oscillator aligned with the maxima and zeros of the lower-frequency oscillator). These examples are mentioned as illustrations of some but not all embodiments of this invention.

When container 1 is vibrated at a frequency with a corresponding wavelength much longer than the container height, the fluid bulk inside is accelerated along with container 1. However, any particles within the fluid are not accelerated directly. The particles, relative to the inertial frame of container 1 and fluid, experience an acceleration opposite the exterior acceleration of container, plus (or minus) the acceleration due to gravity, plus (or minus) the acceleration due to the drag force of the liquid on the particles. If container 1 has a constant acceleration for a long enough period, the particles reach a terminal velocity with respect to container 1. If the acceleration is large enough, the terminal velocity is proportional to the square root of the acceleration of container 1. The total distance traveled with respect to container 1 is almost proportional to the square root of acceleration, multiplied by the time. Container 1 is then accelerated in the opposite direction with a larger acceleration for a proportionately shorter amount of time. The particle now quickly slows down, reverses direction, and reaches a new terminal velocity. After several cycles of alternating acceleration, the velocity and motion of the particle reaches a steady state oscillation.

Since the terminal velocities are not linearly related to the acceleration, the average velocity is not equal to the terminal velocity under gravity. If the higher acceleration (in the inertial frame inside the container) is in the same direction as gravity, the ratio and magnitude of the acceleration can be adjusted to make the average velocity zero, or even opposite the direction of gravity. In other words, the effect of gravity can be negated by the effect of the vibration, and the particle can be levitated inside the fluid.

Figure 2:
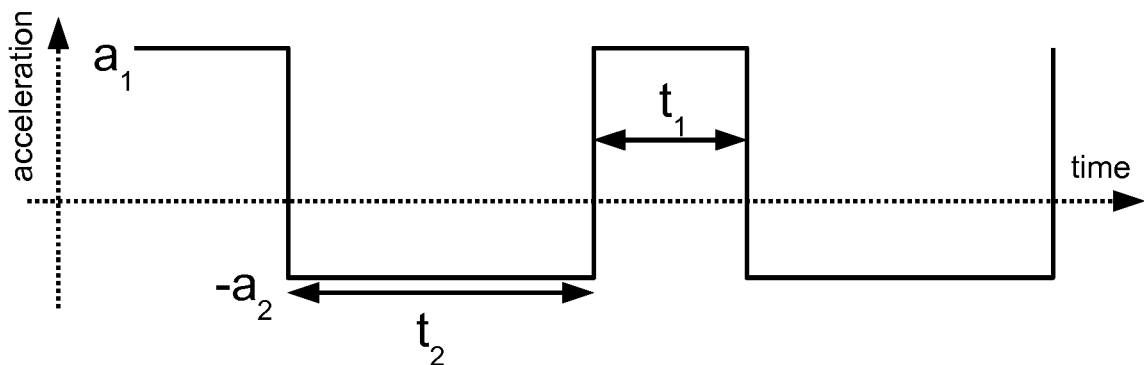
FIG. 2 is an illustration of the velocity of a particle inside a fluid-filled vibrating container accelerated with an ideal rectangular wave.
Figure 2:
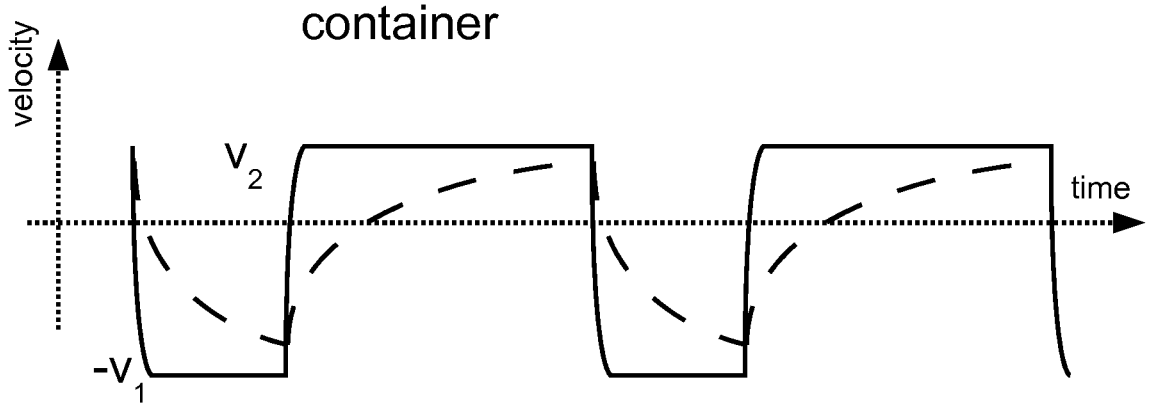

FIG. 2 illustrates the motion of a particle within container 1 accelerated with an ideal rectangular wave. The motion, relative to container 1, of a particle that reaches terminal velocity in much less than a period of vibration similar to the solid line in FIG. 2(b). The average acceleration of container 1 must equal to zero, so:

$$a_1 t_1 = a_2 t_2$$

If the terminal velocities are proportional to the square root of the acceleration (including the acceleration due to gravity, g) then the average velocity can be approximated by this formula:

$$\text{average velocity upwards} = \frac{k}{t_2 + t_1}\left(t_2\sqrt{a_2 - g} - t_1\sqrt{a_1 + g}\right)$$

Thus, to achieve zero average velocity, $$t_2\sqrt{a_2 - g} = t_1\sqrt{a_1 + g}$$

Combining the equations gives $$a_1 = \frac{r^2 + 1}{r - 1}g, \text{ where } r = t_2/t_1$$

$$a_2 = a_1/r$$

For r=2 (i.e, the container is accelerated downwards for twice as long as upwards, at half the acceleration), the accelerations are 5g and 2.5g.

The preceding formulae illustrates an ideal situation. In practical situations, the time periods are too short for terminal velocities to be reached early on in the vibration phase, or even at all, yet levitation can still be achieved, although greater accelerations are needed.

The dashed lines in FIG. 2(b) illustrate the velocity of such a particle. Even though the average velocity (or the total movement) is no longer proportional to the square root of acceleration, it is still less than linearly related. With enough acceleration and/or a long enough period, gravity can still be negated.

Similarly, a perfect rectangular acceleration wave is not practical, but that is not an impediment to levitation. Levitation is possible even with an acceleration wave that is the sum of just two sinusoids, one twice the frequency of the other and in an appropriate phase and amplitude relationship.

Figure 3:
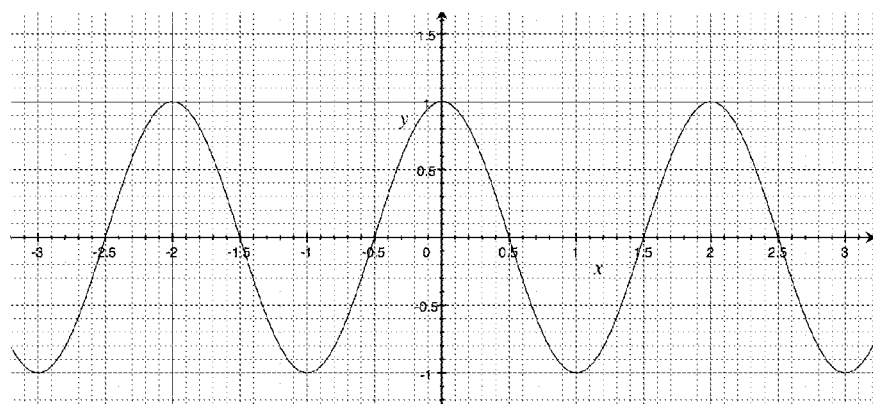
FIG. 3 is an illustration of a waveform that is the sum of two sinusoidal waveforms, approximating a rectangular wave.
Figure 3:
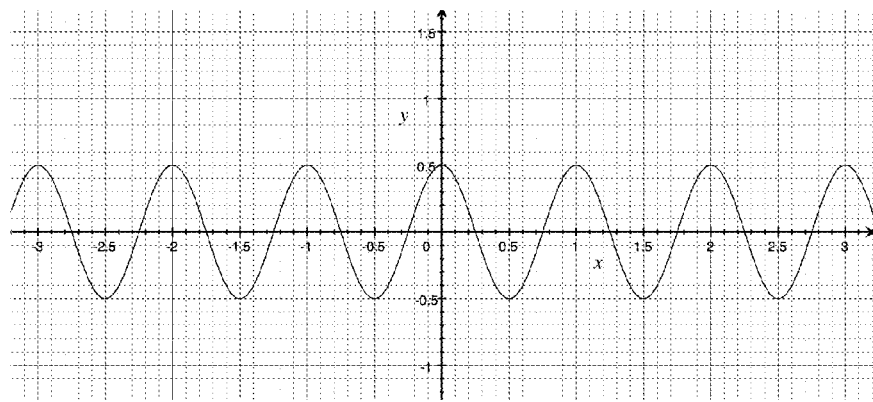
Figure 3:
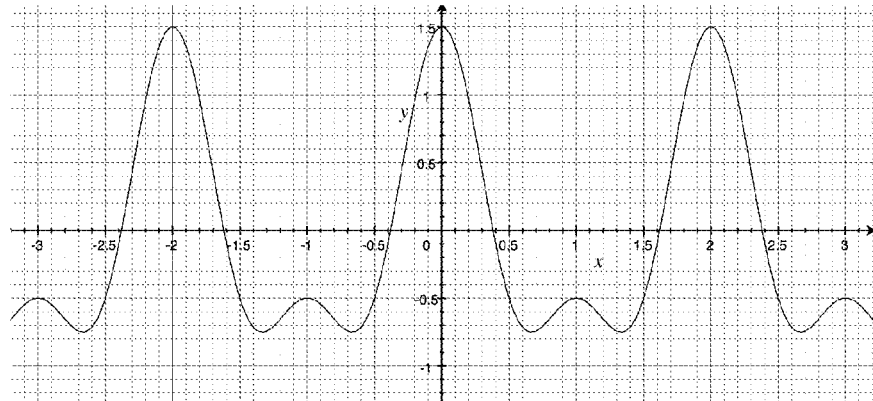

FIG. 3 illustrates such a waveform. Almost any waveform with a shorter period of stronger acceleration upwards and a longer period of weaker acceleration downwards can be used. Furthermore, the acceleration need not even be periodic. A fluctuating waveform, with perhaps a random component, may be desired to increase the movement of the particle. One preferred embodiment makes use of the dual sinusoidal waveform illustrated in FIG. 3, but it is by no means the only form of vibration that can achieve levitation.

Particles can be denser than the fluid and be levitated upwards, or less dense and be levitated downwards, even simultaneously. For example, experiments have levitated glass beads, thin pieces of aluminum, or fine steel shot upwards in water, while air bubbles or hollow glass bubbles were levitated downwards. Bubble column reactors can be improved by being able to levitate and sink bubbles or precisely control the rate they rise.

The acceleration needed to precisely negate gravity varies based on the size, density, shape, and roughness of the particles, the density and viscosity of the fluid, and the shape of the acceleration waveform. Keeping everything else constant, there is a particular size particle at which the least acceleration is required to levitate the particle. For example, numerical simulations (confirmed approximately by physical tests) can predict the preferred size for stainless steel spheres in water, vibrated at about 30 cycles per second, with upwards acceleration twice downwards. The preferred size of the spheres is approximately 0.05 to approximately 0.3 mm, more preferably about 0.135 mm in diameter. The preferred size for spherical air bubbles in water under the same conditions is approximately 0.2 to approximately 1 mm in diameter, and more preferably about 0.5 min in diameter; however, the air bubbles deform under pressure so the spherical approximation is inaccurate. Particles shaped to have higher inertial drag are easier to levitate (requiring less acceleration), since they will reach terminal velocity faster, and inertial drag will dominate over viscous drag at a lower velocity. Thus, spheres are harder to levitate than longer, but thinner, pieces of wire of the same density and mass, and thin sheets are easier to levitate than thicker sheets.

Multiple particles can be levitated at the same time, even though the interactions between particles complicates the process. The vibrations or other particles may break up particles into smaller particles, which often makes levitation easier. For example, large air bubbles in water break up from the drag force of the water, similar to the breakup of large raindrops falling through the atmosphere, and the smaller bubbles can be easier to levitate downwards. Bubbles of air or other fluid can also be broken up further by solid particles (whether the solid particles are fully levitated or not). A large number of solid particles can be levitated and fluidized, without needing ultrasonic frequencies or the circulating fluid that other fluidization techniques require. The interactions between particles can affect the amplitude of acceleration required to levitate the particles. Computational fluid dynamics can be used to model the effect, or the effect can be determined through empirical research. The interactions between particles often create beneficial side effects. For example, particles are affected by other particles' wakes, causing particles to "kiss" when one is upstream of another and close enough (e.g. within about two to three diameters for spherical particles). Particles may temporarily agglomerate, or interact in other ways. These effects can occur at relatively modest concentrations. For example, a particle concentration of about just 1% by volume results in an average spacing of about 2.7 diameters between spherical particles, a distance which is close enough for inter-particle interactions.

The agglomeration and/or "kissing" of particles can bring about homogeneous nucleation. Agglomeration results in local supersaturation, and "kissing" brings molecules into direct contact, both of which can help nucleation. Vibrations can aid in crystallization, but it is not known if the effect can be achieved at such low frequencies as embodiments the present invention make possible. Furthermore, embodiments of the present invention increase uniformity by vibrating the entire fluid the same amount throughout the volume of the container. Prior to or during vibrations, the fluid can be supercooled, or antisolvent can be added, or solvent can be removed, to achieve supersaturation and nucleation.

Researchers have proposed that cavitation plays a role in homogenous nucleation. However, cavitation is not necessary. Homogeneous nucleation can be achieved by ultrasound that is of low enough power not to cause cavitation. One mechanism that encourages nucleation when cavitation is not present is inter-particle interaction brought about by the draft caused by the velocity of the particles relative to the bulk fluid.

Cavitation

Compressible bubbles (or any portion of the container that does not form a rigid barrier) at one end of the container can cause cavitation at the opposite end of container, if the pressure drops below a certain value. This value is generally the vapor pressure of the liquid, but can vary depending on other factors such as the gas or solid content in the liquid. (Cavitation may also occur if the height of the container is close to or larger than the wavelength of the vibration in the fluid.) Cavitation occurs when the change in liquid pressure due to the acceleration downwards (minus g) and height of liquid is greater than the initial pressure inside the container less (approximately) the vapor pressure of the fluid. Thus, there are several parameters which can be modified to avoid or create cavitation, including the presence, absence, or location of bubbles, average pressure inside the container, height of the container, density of the fluid, and the frequency, amplitude, and shape of the vibration waveform.

Maintaining a high enough average pressure inside the container can avoid cavitation. For example, at standard atmospheric pressure, and a peak downward acceleration of about 30g, cavitation can be avoided within a container up to approximately one foot in height. Cavitation can also be avoided at even lower pressures or higher accelerations in a rigid container with no compressible bubbles or other particles, or with large enough compressible and expandable bubbles at both ends, as these existing bubbles expand with pressure changes, preventing the formation of new bubbles.

Cavitation can be easily achieved, if desired, by reducing the pressure inside the container. This reduction of pressure can be accomplished simply by cooling the fluid inside a sealed container, which can drop the pressure as low as the vapor pressure of the fluid, thereby creating bubbles of vapor or of any previously dissolved gasses. Therefore, it is preferable to control the temperature of a rigid sealed container, and if cavitation is to be avoided, the container can be sealed at high pressure or at a temperature safely below its operating temperature. Pressure inside the container can also be controlled dynamically to prevent or enable cavitation as desired.

When the pressure is low enough for cavitation, the shape of the vibration waveform can be adjusted as described above to levitate bubbles to prevent cavitation, or the waveform can be inverted to inhibit negative buoyancy, keeping the bubbles at the top, to increase cavitation, while keeping the frequency and amplitude the same. The shape of the bottom of the container is preferably curved or conical to stabilize the location and shape of cavitation bubbles.

Cavitation is the nucleation and collapse of bubbles (cavities) within a liquid, caused by rapid changes in pressure. Sinusoidal vibrations can bring about cavitation collapse that is even more rapid than the rate of change of pressure because of non-linear effects. Non-sinusoidal vibrations can increase or decrease the speed of cavitation. This can be accomplished with the addition of higher harmonics to the vibration to create a wave similar to a square wave or a sawtooth wave. A square wave or the correct polarity of a sawtooth-like wave may increase the speed of cavitation, while the opposite polarity can decrease it. The best waveform for maximizing or minimizing the speed of cavitation collapse may depend on many factors, including but not limited to the limitations of the vibration driver.

A bubble can also be levitated at one vibration frequency while a second sonic source at a faster frequency induces cavitation. The frequency of the second sonic source can be tuned to the bubble's natural frequency, which is a function of the bubble's size. This allows the use of a wider range of bubble sizes and frequencies than has been possible.

The present invention is well suited for research into cavitation. Since the present invention can produce cavitation at low frequencies (for example, tens of hertz or even lower), with relatively large bubbles of a diameter exceeding a millimeter, observation and measurement of the cavitation process is much easier than with ultrasonic cavitation with much smaller bubbles.

Horizontal and Multidimensional Vibrations

In another embodiment of the invention, the container is vibrated horizontally to separate or improve the mixing of particles. For example, a bubble column reactor can be vibrated horizontally in a way that moves bubbles to the right and dense particles to the left, separating the bubbles from the particles, if separation is desired. When mixing is desired, the vibration can be inverted repeatedly, causing lighter and heavier particles to switch places, mixing the particles horizontally across the entire width of the container, thus increasing the reaction rate, mass transfer rate, heat exchange, diffusion rate, or the rates of other processes. Similarly, the shape and/or amplitude of vertical vibrations can be fluctuated to improve vertical mixing.

Vibrations can also be applied in three dimensions simultaneously, or the axis of vibration can be rotated. Within a microgravity environment such as earth orbit, this allows full levitation of a particle and the ability to counteract residual acceleration. Fluctuating the shape of the vibrations in three dimensions or rotating the vibration axis will mix particles in three dimensions.

An embodiment of the present invention includes vibration of an entire container, instead of just one wall or the insertion of an ultrasonic probe, the vibration is substantially uniform throughout the container. This uniformity has several advantages. Reaction speeds, temperature, concentration, and pressure may be all be more uniform throughout the container.

Thermal Convection

One embodiment of the present invention can also be used to eliminate or reverse thermal convection in fluids. Vibrations of the type described can cause a cold layer of fluid at the bottom of the container to stream up through warmer fluid to the top of the container. This effect has been demonstrated using thermochromic pigment in a liquid heated at top and cooled at the bottom. In a slow motion video, the cooler liquid rose under the influence of the vibrations. The ability to slow or reverse convection can improve chemical processes such as crystallization, solidification, and combustion.

The reduction or elimination of convection in gas can also be achieved. This can improve combustion processes, but, if the amplitude of vibration is high, the location of the flame must be moved along with the motion of the hot gas, or the flame can fluctuate in intensity or be extinguished. A second source of vibration or a lever system is needed to keep the flame location in sync with the motion of the hot gas.

Colloids, Alloys, and the Like

Another application of embodiment of the present invention is rapid mixing of two or more immiscible fluids of different densities to create colloids. As the vibration is increased, ripples form and grow at the interface between the fluids, eventually becoming large enough that bubbles of one fluid can be entrained in the other fluid. If the vibration was purely sinusoidal, the bubbles would tend to settle back, but when the vibration is non-sinusoidal as described above, bubbles of the right size can be levitated further into the other liquid. As the vibrations continue, larger bubbles break into smaller bubbles, until the aggregation rate (the rate that bubbles collide with each other and form large bubbles) substantially equals the rate that the vibrations break up bubbles. A colloid can be quickly produced with a wide range of vibration frequency, from a few cycles per seconds up to ultrasonic frequencies. The colloid will persist as long as the vibration is maintained. The frequency, shape, and amplitude of the vibration can be adjusted to change the size of the droplets, potentially making droplets small enough to maintain stability of the colloid long after the vibrations cease. Stabilizers can also be added to improve stability.

One example of this embodiment is in the production of ice cream and other frozen desserts. Cream, flavoring syrup, and air can be thoroughly mixed at room temperature and frozen afterwards. The colloid mixture can be stable enough and fine-grained enough to be frozen slowly by storing the container with the mixture in a freezer, with the result being a smoothly textured ice cream with small ice crystal grains. This technique has several advantages over the traditional method of churning while cooling. First, the mixing device does not need to be cooled. Second, the container that the ice cream is mixed in can also be the container that it is shipped and/or served or sold in, in which case no equipment cleaning is necessary between the manufacture of different flavors. Freezing can even be done during delivery, such as in freezer trucks, and possibly delayed until after delivery, decreasing the risk of melting.

Another application is in the production of alloys or solidified colloids that quickly separate after vibrations are stopped. Two or more fluids can be mixed into a fine colloid and vibrations continued during a cooling process to solidify the mixture. The frequency and amplitude of the vibrations can be adjusted to adjust the size of the grains of the different materials. This technique can be used to create new or improved alloys, solid foams, and similar materials.

Fluidized Bed and Bubble Column Reactors

Compared to the flow rate of a fluidized bed reactor, an embodiment of the present invention can achieve higher velocity of particles relative to the fluid. For a fluidized bed, there is one flow rate (or a narrow range of rates) that fluidizes particles, but the vibration amplitude and frequency of the present embodiment can be adjusted over a wide range, as the shape of the waveform can be adjusted to maintain levitation. For example, the amplitude of the second harmonic can be adjusted relative to the first harmonic to achieve fluidization. Furthermore, embodiment does not require a recirculating path for the fluid.

Bubble column reactors, including water treatment applications, can also be improved or replaced with the embodiment. Researchers have found that sinusoidal vibrations can increase mass transfer rates in bubble column reactors. They have also noted that the rise of bubbles can be slowed by sinusoidal vibrations. They have not however, discovered how the rise of bubbles can be completely stopped or even reversed through non-sinusoidal vibrations. Besides speeding up mass transfer rates, using non-sinusoidal vibrations to levitate the bubbles can increase the utilization of gas and allow the use of shorter bubble columns.

Vibration Testing

Vibration testing can also be improved with embodiments of the present invention. Current vibration testing standards only require sinusoidal vibrations, swept sine tests, random tests, and/or impulse tests. However, as shown above, significant effects can occur with periodic but non-sinusoidal vibrations, even by adding just a second harmonic, that has never been seen with a sinusoidal waveform or a random waveform. Vertical vibrations can cause particles to levitate in a less dense fluid and even collect at the top, while horizontal vibrations can cause horizontal streaming, amongst other effects.

In particular, battery testing can be improved with embodiments the present invention. Batteries depend on a predictable, stable movement of ionic particles across an electrolytic fluid, and thus are particularly sensitive to vibrations that affect this movement. The need for thorough vibration testing is even more important if the batteries will be subjected to external changes of pressure and/or temperature. Non-sinusoidal vibrations can cause damage that will not be exposed through any amount of sinusoidal or random vibration testing. Cavitation can occur, especially if gas bubbles form inside the battery due to a drop in pressure, which can be caused by a drop in temperature. If the battery container has a vent, vibrations or heat could cause the battery to vent, dropping the pressure inside the battery, and, after cooling, vapor bubbles can form inside the battery. Non-sinusoidal vibrations can also affect the flow of electrolyte, causing the concentration of electrolyte and ions to vary within the battery. Non-sinusoidal vibrations can also reduce or increase convection, which can cause the battery to overheat. Vibration can also cause ion particles to flow faster across the electrolyte solution, causing spikes in current. Non-sinusoidal vibrations can inhibit or increase ionic movement in one direction, increasing or decreasing the current supplied or needed for charging. Vibrations may also cause the electrolyte and ions to dump due to the effect of drafting. For all these reasons, it is preferable to vibration test lithium or other highly hazardous batteries using a non-sinusoidal waveform (such as the waveform in FIG. 3c composed of the first and second harmonic), while fluctuating temperature and pressure across the full range that may be encountered in actual use.

In one embodiment, the vibration testing method includes several steps, which may be repeated for thoroughness or to check for long-term behavior. The first step, which may be optional for some tests, is to decrease the pressure inside of the fluid environment so that vapor or gas bubbles are formed, or to make cavitation more likely in later steps. This can often be accomplished simply by cooling the fluid (and keeping the fluid cool through later steps) inside a sealed container. Alternatively, the container can be vented, the pressure reduced, and the container can be resealed, with a small amount of gas bubbles allowed to replace some of the fluid. If the container under test has a built-in venting mechanism to reduce fluid in case high pressure builds up inside the container (such as the vent on some lithium batteries), heating the fluid, vibrating the container, or reducing the pressure outside of the vent, may reduce the pressure inside by forcing or suctioning out some of the fluid inside the container. Then, the temperature of the fluid can be returned to normal.

The next step in vibration testing is to vibrate the container over a sufficient period of time with different sinusoidal and non-sinusoidal waveforms along the axes of interest. In particular, at least three or four different waveforms can be tested at each desired frequency. Along a vertical (or partially vertical) axis, one waveform can be sufficiently non-sinusoidal to cause the flow of small bubbles downward and small heavier-than-fluid particles upwards. A waveform that is the sum of the first and second harmonics, as illustrated in FIG. 3, is one embodiment. The same or similar waveform but inverted is another waveform for testing. This waveform can inhibit the negative buoyancy effect of sinusoidal vibrations on entrained bubbles, and prevent the rise of heavier particles due to vibrations. Such a waveform can be important for testing the long-term effect of cavitation collapse. Entrained bubbles that sink due to the negative buoyancy effect of sinusoidal vibrations on compressible bubbles may interfere or prevent cavitation because those bubbles may grow and shrink from the pressure changes, instead of the cavitation growth and collapse of new bubbles. (This is another reason why a pure sinusoid is not a preferred test waveform by itself, as a sinusoid may cause only a brief amount of cavitation at the initiation of the vibration, which will stop after just a few cycles once the entrained bubble has dropped to the bottom half of the fluid.) A third type of waveform for testing is one which is just non-sinusoidal enough to levitate some bubbles or particles throughout the container. It may be desirable to modulate this waveform somewhat to ensure a sufficiently wide range of levitation and mixing. Furthermore, different waveforms or amplitudes may be used to levitate different types and sizes of particles or bubbles. Optionally, repetitive shock testing can also be performed, both upwards and downwards, preferably at a sufficient amplitude to cause cavitation (although shock testing can be considered a subset of the non-sinusoidal tests already mentioned). Finally, a pure sinusoidal vibration can be tested as well. Similar tests can be done on horizontal axes to test the possibility that non-sinusoidal vibrations can bring about bulk movement. Furthermore, horizontal vibration testing may be important for batteries or other devices that have fluid sandwiched between solid vertical components or plates, as horizontal vibrations may affect the rate of horizontal movement and diffusion of the fluid and particles between the vertical plates.

In all these tests, the preferred waveform is the actual vibration of the innermost container containing the fluid, not the power applied to the transducer or the vibration of the testing apparatus in the absence of the test item or the vibration of any outer container. If the container or fluid to be tested is part of a larger object, and it is necessary or desirable to vibrate the larger object instead of the container itself, then it may not be possible or practical to measure or know the actual vibration waveform that the container experiences. In such a case, more waveforms can be tested, varying the phase and/or amplitude of the second harmonic (and possible higher harmonics) to ensure that the inner container experiences all vibration waveforms of interest. For example, a single battery may contain several individual cells inside of an outer case, and it may be desirable to test the entire battery instead of the individuals cells to test the heat dissipation or other interactions between cells. If the cells are not firmly attached to the outer case, the cells may vibrate with a differently shaped waveform than the entire battery. Preferably an accelerometer or audio transducer can be attached to the interior cell or cells and used as the reference waveform. If that is not possible, but the vibration response of the interior cells to the exterior battery vibration is known, then the vibration of the battery can be adjusted to produce the desired vibration of the internal cells. If the vibration response is not known, then a variety of waveforms should be tested. A suitable waveform can often be found by slowly sweeping the phase and amplitude of the second harmonic while looking for a non-linear response from an acoustic transducer or other sensor that often indicates cavitation or other non-linear effects that can cause damage.

Tests can be repeated at different temperatures and pressures across the entire range of operation, particularly at lower temperatures and pressures, and the transition from one temperature and/or pressure to another can increase the likelihood of cavitation, as explained above.

Each of the waveforms can be applied for a sufficient amount of time to allow for cumulative effects. Optionally, testing can also alternate or cycle through short periods of the different waveforms, to test whether the transitions cause damage or failure.

One embodiment includes an acoustic transducer or other sensor to detect acoustic waves caused by cavitation collapse or other non-linear response to the vibrations. In particular, cavitation and other effects may only occur at the initiation or end of application of each waveform or transitions between waveforms. The test procedures can make note of any anomalies which can be evidence of cavitation collapse and those test conditions can be repeated to check for the accumulation of damage.

If the object to be tested is part of a larger system, it is preferred for the testing to occur under conditions as close to normal operation as possible, and its performance under vibration compared to its performance without vibration. For example, if the test object is a battery, it is preferably tested within a circuit or charger that simulates normal usage, and the voltage and current waveforms when subjected to vibrations can be compared to the waveforms without vibrations. After the test, the interior of the battery subjected to vibrations can be inspected against a battery that underwent the same test without vibrations.

If damage from vibrations is found, then the object under test may be redesigned with internal or external vibration damping mechanisms. Alternatively, or in addition, a vibration sensor may be added to detect dangerous vibrations and/or the occurrence of cavitation collapse or other potentially damaging conditions. If pressure and/or temperature variations or other variables are also shown to take a role in the risk of failure, then those may be controlled and/or recorded by sensors.

Improving Batteries

Another object of the present invention is an apparatus, and method to increase the current that a battery cell can supply, or the charging speed of a battery cell, through the application of sinusoidal or non-sinusoidal vibrations. Horizontal sinusoidal vibrations increase the flow of electrolyte and ions between vertical electrodes, reducing the internal resistance of the cell and increasing the maximum current, both for charging and discharging. Non-sinusoidal horizontal vibrations can cause ions to migrate in a specific direction. If the direction between the cathodes and anodes is the same throughout the cell, such as in a bipolar battery, then this migration may improve charging at the expense of discharging, or vice-versa, depending on the polarity of the vibration waveform. A large enough vibration amplitude may even be enough to charge the cell or reduce the voltage required for charging. Vibration can be dynamically increased or decreased, or eliminated entirely, depending on the current required. This flexibility allows a larger separation between electrodes, increasing safety by reducing risk of an internal short circuit and the ability to stop thermal runaway by stopping vibrations.

Ultrasound

Another application of the present invention is in the field of medical ultrasound. The shape of the ultrasound waveform can be adjusted to induce streaming while keeping the risk of cavitation or tissue heating low. U.S. Pat. No. 5,523,058 (issued Jun. 4, 1996 to Shinichiro Umemura) disclosed an ultrasonic apparatus that combines the first and second harmonic, but described the effect as increasing cavitation. Although cavitation may also be somewhat increased, much of their observed effect was likely due to the streaming or mixing effect of non-sinusoidal vibrations on particles of different sizes, shapes, or densities. Adding odd harmonics instead of the second harmonic, at the proper phase and amplitude relationship (to approximate a square pressure wave, as an example) may increase cavitation without causing streaming, unless passing through tissue or bubbles that have a sufficient non-linear response to the ultrasound. Conversely, adding harmonics with the correct phase and amplitude relationship, possibly by approximating a triangle pressure wave or the right polarity of a sawtooth wave, can reduce cavitation by reducing the maximum rate of change of pressure. Reducing the risk of cavitation may make ultrasound safer.

These same principles can be applied to the use of non-medical ultrasound. The ultrasonic waveform can be shaped and varied to control the amount of cavitation and the amount of mixing, streaming, and levitation.

A further consequence of this invention is the realization that there may be a need for a third metric for estimating the level of safety of medical ultrasound, in addition to the Thermal Index (TI), and the Mechanical Index (MI). This new metric can provide a better measure of the likelihood of streaming and/or mixing caused by non-sinusoidal vibration, and can be computed from the amplitude of the second harmonic (or other even harmonics) measured in the reflected wave. Also, as additional harmonics are added (or caused by non-linear response to a sinusoidal wave), the definition of MI and possibly TI may be adjusted.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed is:

1. A method of providing asymmetric oscillations on a container, the method comprising:
   disposing a fluid and a particle in the container;
   imparting oscillations having an asymmetric waveform to the particle through the fluid by way of a vibration driver attached to the container, wherein the fluid exerts a non-linear drag force responsive to the asymmetric waveform of the oscillations;

controlling, via a controller coupled with the vibration driver, the imparted oscillations to adjust the non-linear drag force exerted by the fluid on the particle using non-sinusoidal vibrations;

sensing a plurality of effects of the oscillations of the particle via a plurality of sensors disposed on the vibration driver and coupled with the controller, where each of the plurality of sensors detects and measures a different one of the plurality of effects of the oscillation on the particle;

receiving, at the controller, a feedback signal from at least one of the plurality of sensors regarding a measurement corresponding to at least one of the detected plurality of effects;

analyzing the feedback signal to determine a type and a degree of adjustment of the oscillation required to achieve a desired effect on the particle; and outputting a second signal to adjust an asymmetric characteristic of the oscillation in accordance with the determined type and amount of adjustment based on the feedback signal analysis.

2. The method of claim 1, wherein the particle is one of a plurality of solid particles in the fluid, and further comprising breaking up gas bubbles, liquid bubbles, or other solid particles within the fluid using the plurality of solid particles.

3. The method of claim 1, wherein the asymmetric waveform of the imparted oscillations are controlled so as to cause homogenous nucleation.

4. The method of claim 1, further comprising supercooling the fluid.

5. The method of claim 1, further comprising adding an antisolvent.

6. The method of claim 1, further comprising removing a solvent.

7. The method of claim 1, further comprising providing a non-rigid portion at an end of the container.

8. The method of claim 1, further comprising changing pressure inside the container.

9. The method of claim 8, wherein changing the pressure comprises changing the temperature of the fluid.

10. The method of claim 1, wherein controlling the imparted oscillations resulting in upward or downward movement of bubbles.

11. The method of claim 1, wherein the container comprises a shaped end that stabilizes a location of cavitation bubbles.

12. The method of claim 1, wherein controlling the imparted oscillations comprises providing that the asymmetric waveform has a sawtooth shape that increases a speed of cavitation implosion of bubbles within the fluid.

13. The method of claim 1, wherein the asymmetric waveform comprises a first frequency for levitating a bubble of gas in the fluid and a second frequency that is faster than the first frequency to induce cavitation implosion of the bubble.

14. The method of claim 13, wherein the second frequency is a natural frequency of the bubble.

15. The method of claim 1, wherein the oscillations are horizontal along an axis that is orthogonal to gravity.

16. The method of claim 15, wherein the horizontal oscillations cause horizontal separation among particles in the fluid.

17. The method of claim 15, wherein the horizontal oscillations cause horizontal mixing of particles in the fluid.

18. The method of claim 1, wherein the oscillations are vertical along an axis that is parallel to gravity.

19. The method of claim 1, wherein controlling the imparted oscillations comprises varying the asymmetric waveform to mix particles in the fluid.

20. The method of claim 1, wherein the oscillations are imparted along a plurality of axes of different dimensions simultaneously.

21. The method of claim 1, wherein imparting oscillations to the particle comprises imparting the oscillations along an axis at a first position, and further comprising rotating the axis to a second position.

22. The method of claim 1, further comprising placing the container in a microgravity environment.

23. The method of claim 1, wherein imparting oscillations comprises eliminating or reversing thermal convention in the fluid, and further comprising moving a location of a flame in sync with the fluid.

24. The method of claim 1, wherein the fluid is an immiscible fluid having a first density, and further comprising disposing another immiscible fluid having a different density in the container, wherein the imparted oscillations mix the two immiscible fluids to create a colloid.

25. The method of claim 1, further comprising:
mixing air into the fluid at room temperature; and
freezing the fluid after the air has been mixed into the liquid.

26. The method of claim 1, wherein the oscillations are imparted at a freezing temperature.

27. The method of claim 1, further comprising cooling the fluid while imparting the oscillations to produce alloys or solidified colloids.

28. The method of claim 1, wherein the container is a fluidized bed reactor.

29. The method of claim 1, wherein the container is a bubble column reactor.

* * * * *